(12) United States Patent
Timmermans (10) Patent No.: US 9,011,962 B2
(45) Date of Patent: Apr. 21, 2015

(54) BOVINE MEAT COMPOSITIONS HAVING ENHANCED QUALITY, NUTRITIVE AND HEALTH VALUES OBTAINED FROM ENRICHMENT DIETS

(76) Inventor: Simon J. Timmermans, Sibley, IA (US)

( * ) Notice: Subject to any disclaimer, the term of this patent is extended or adjusted under 35 U.S.C. 154(b) by 582 days.

(21) Appl. No.: 13/398,990

(22) Filed: Feb. 17, 2012

(65) Prior Publication Data

US 2012/0164308 A1    Jun. 28, 2012

Related U.S. Application Data

(63) Continuation of application No. 12/201,496, filed on Aug. 29, 2008, now Pat. No. 8,142,816.

(60) Provisional application No. 60/968,582, filed on Aug. 29, 2007.

(51) Int. Cl.
| | | |
|---|---|---|
| *A23L 1/31* | (2006.01) | |
| *A23K 1/18* | (2006.01) | |
| *A23K 1/16* | (2006.01) | |
| *A23K 1/175* | (2006.01) | |
| *A61K 35/00* | (2006.01) | |

(52) U.S. Cl.
CPC ............ *A23K 1/1813* (2013.01); *A23K 1/1603* (2013.01); *A23K 1/1631* (2013.01); *A23K 1/1758* (2013.01); *A61K 35/00* (2013.01)

(58) Field of Classification Search
None
See application file for complete search history.

(56) References Cited

U.S. PATENT DOCUMENTS

| | | | |
|---|---|---|---|
| 4,847,087 | A | 7/1989 | Young |
| 5,770,247 | A | 6/1998 | Satter et al. |
| 6,045,834 | A | 4/2000 | Howes et al. |
| 6,288,114 | B1 | 9/2001 | Bauman et al. |
| 6,602,537 | B1 | 8/2003 | Cummings et al. |
| 6,962,718 | B2 | 11/2005 | Ramackers |
| 7,014,874 | B1 | 3/2006 | Majeed et al. |

FOREIGN PATENT DOCUMENTS

CA    2 514 896 C    9/2004

OTHER PUBLICATIONS

Clark, LC, et al., "Effects of selenium supplementation for cancer prevention in patients with carcinoma of the skin" Journal of the American Medical Association, 276:1957-1963, 1996.
Clover, Charles, "Why eating a game old bird can lift your mood" Advertisement GMT Dec. 25, 2006, 3 pages.
Clyburn, B.S., et al., "Effect of selenium source and vitamin E level on performance and meat quality of feedlot steers", Texas Tech University, 16 pages.
Combs, Jr., Gerald F., "Symposium: Nutrient Disease Relationships: Closing the Scientific Knowledge Gap", American Society for Nutritional Sciences, 2005, pp. 343-347.
Ackson, Malcolm J., et al., "Are there functional consequences of a reduction in selenium intake in UK subjects", Proceedings of the Nutrition Society, 2004, 63, pp. 513-517.
Henry, Pamela R., et al., "Selenium Bioavailability" Department of Animal Science, University of Florida, Bioavailability of Nutrients for Animals: Amino Acids, Minerals and Vitamins, 1995, pp. 303-336.
Loneragan, Guy H, et al., "Trends in mortality ratios among cattle in US feedlots", Scientific Reports: Original Study, JAVMA, vol. 219, No. 8, Oct. 15, 2001, pp. 1122-1127.
Lyons, T.P. et al., "Science and Technology in the Feed Industry", Proceedings of Alltech's Seventeenth Annual Symposium, pp. 377-392.
Maas, John, "Studies on selenium metabolism in cattle: Deficiency, supplementation, and environmental fate of supplemented selenium", STDA Sixth International Symposium, May 10-12, 1998, Scottsdale, pp. 139-147.
Murphy, Janice, "Is There a Market for Selenium-Enriched Pork?", Ontario, Ministry of Agriculture, Food and Rural Affairs, www.omafra.gov.on.ca/english/livestock/swine/facts/info_sel.htm, 3 pages.
Pavlata, L., et al., "Blood and Tissue Selenium Concentrations in Calves Treated with Inorganic or Organic Selenium Compounds—A Comparison", ACTA VET. BRNO 2001, 70:19-26.
Rayman, Margaret P., "The importance of selenium to human health", The Lancet, vol. 356, Jul. 15, 2000, pp. 233-241.
Sandoval, M., et al., "Relative bioavailability of supplemental inorganic zinc sources for chicks" J. Animal Science, 1997, 75:3195-3205.
Schrauzer, Prof. Gerhard N. et al., "Facts putting an end to selenium controversy", Selenium Controversy, Aug. 20, 2003, 2 pages.
Schrauzer, Prof. Gerhard N., "Selenomethionine: A Review of Its Nutritional Significance, Metabolism and Toxicity", Recent Advances in Nutritional Sciences, Department of Chemistry and Biochemistry, University of California, pp. 1653-1656.
Simek, Jaroslav et al., "Selenium content of beef and its effect on drip and fluid losses", Animal Science Papers and Reports, vol. 20 (2002) Supplement 1, 49-53.
"Petition for Health Claims: Selenium and Reduction in the Risk of Certain Cancers; Selenium and Anticarcinogenic Effects" Submitted to the Food and Drug Administration, Jul. 10, 2002, Petitioner: Wellness Lifestyles, Inc., pp. 1-21.

*Primary Examiner* — Tekchand Saidha
*Assistant Examiner* — Md. Younus Meah
(74) *Attorney, Agent, or Firm* — McKee, Voorhees & Sease, P.L.C.

(57) ABSTRACT

The present invention relates to improved meat products produced by novel methods of increasing the selenium and Vitamin E content in beef by feeding special enriched diets. The present invention further provides improved meat products having increased Vitamin E retention, reduced TBARS and/or improved water holding capacity in comparison to meat products not obtained from beef cattle fed said special enrichment diet.

13 Claims, 8 Drawing Sheets

BOVINE MEAT COMPOSITIONS HAVING ENHANCED QUALITY, NUTRITIVE AND HEALTH VALUES OBTAINED FROM ENRICHMENT DIETS

CROSS-REFERENCE TO RELATED APPLICATIONS

This application claims priority as a continuation application to U.S. application Ser. No. 12/201,496, now U.S. Pat. No. 8,142,816, filed on Aug. 29, 2008, which claimed priority under 35 U.S.C. §119 to provisional application Ser. No. 60/968,582 filed Aug. 29, 2007, herein incorporated by reference in its entirety.

BACKGROUND OF THE INVENTION

Field of Selenium Use in Humans

Selenium is a chemical element with atomic number 34 and chemical symbol "Se." Selenium occurs rarely in the free-state in nature. It is a nonmetal that is chemically related to sulfur and tellurium. Although selenium is toxic in large amounts, it is considered an essential trace element and essential micro-nutrient for both animals and humans. Selenium is essential to form the active center of certain enzymes necessary for the function of all cells in both humans and animals. Selenium requirements in plants, animals and humans differ by species.

In humans, selenium is a trace element nutrient which functions as a cofactor for reduction of antioxidant enzymes such as glutathione peroxidases and thioredoxin reductase. However, ongoing research has identified that selenium has a physiological role involving enzymes in addition to the glutathione peroxidases. Selenium plays an important role in non-antioxidants' functions as well. For example, selenium also plays a role in the functioning of the thyroid gland by participating as a cofactor for thyroid hormone deiodinases. Selenium is also critical to immunocompetence as well as reproductive and other physiological functions of the body. However, the majority of research focuses on selenium's effectiveness as an antioxidant. Such protection is critical so that intracellular environments of all cells are protected from oxidants and allow enzymatic functions to protect the body.

Research focusing on the supplementation of human diets with selenium is a result of the finding that selenium is an essential trace element with numerous health benefits directly related to a person's dietary intake of selenium. Perhaps most importantly, selenium is a part of the antioxidant enzyme system in the body. Selenium works with other functional proteins in the body to ensure that toxic free radicals and peroxides formed intracellular remain neutralized to prevent cellular damage and numerous diseases, including cancers.

Despite this increase in evidence showing the importance of selenium in the human diet, it is apparent that humans are becoming increasingly selenium deficient. This is caused by a variety of factors, including the fact that soils in many regions where livestock are grown are either low in selenium content or selenium-deplete. As a result, crops grown in such soil have a lower selenium concentration and the animals that feed off of such crops are often selenium deficient. Ultimately, low selenium levels in crops and animals results in decreased selenium intake through animal products that humans consume.

Table 1 shows the impact of selenium contact in the soil and the resulting impact on cattle raised in these areas. Research has focused on how cattle raised on soils containing different levels of selenium can impact the levels found in the meat. It is concluded that high soil levels will increase the naturally occurring organic selenium levels in forage grown and be transferred to the animal.

TABLE 1

| Ingredient | Diet Se Level, mg/kg | Muscle Se Level, mg/kg |
| --- | --- | --- |
| Hintze et al. (2002) | High area | 2.10 |
| | Low area | 0.40 |
| | High/low/0.62 | 1.20/0.35 |
| | High/low/11.9 | 2.06/1.50 |

Such depletion of selenium and resultant decreased intake of selenium is significant as several studies have suggested a link between cancers in humans and selenium deficiencies. FIGS. 1-4 demonstrate the direct correlation between selenium levels in humans and types of cancer. This link between selenium content and various forms of cancer results from the association between neutrophils and other phagocytic cells and a human's selenium status. Additional, studies have shown that selenium is active in mammary glands against mastitis pathogens, is active in the lungs against respiratory pathogens, and is also active in utero against foreign bacteria, placental membranes postpartum and against other phagocytic cells in the body. (See Combs, American Society for Nutritional Sciences, 2005).

Studies on the effect of selenium supplementation related to the recurrence of skin cancers did not demonstrate a reduced rate of recurrence of skin cancers; however the results did show a significantly reduced occurrence of total cancers. (See L. C. Clarke et al. JAMA, 276:1957-1963, 1996). Clarke observed that approximately 200 mcg of selenium supplemented in a chemically organic form derived from selenium yeast are required per day to receive anticancer effects of the trace mineral. Additionally, dietary selenium has been shown to prevent chemically induced carcinogenesis in rodent studies.

Selenium may help prevent cancer by acting as an antioxidant or by enhancing immune activity. The Food and Drug Administration ("FDA") also acknowledges the potential anticancer benefits of selenium by allowing the following claims to be made regarding selenium:

Claim 1:
"Selenium may reduce the risk of certain cancers. Some scientific evidence suggests that consumption of selenium may reduce the risk of certain forms of cancer. However, FDA has determined that this evidenced is limited and not conclusive."

Claim 2:
"Selenium may produce anticarcinogenic effects in the body. Some scientific evidence suggests that consumption of selenium may produce anticarcinogenic effects in the body. However, FDA has determined that this evidence is limited and not conclusive."

(FDA Health Claim Petition: Selenium and Reduced Risk of Certain Cancers and Selenium and Anticarcinogenic Effects (FDA Docket No. 02P-0457)).

The treatment and prevention of cancer represent a significant public health concern within the United States and throughout the world. Cancer remains the second-leading cause of death within the United States alone. The American Cancer Society, Cancer Facts and Figures estimates that one of every four deaths in the United States is a result of cancer.

Accordingly, there is an ongoing long-felt need in the public health community for cancer treatments and preventions, and to decrease one's risk of developing various forms of cancers.

Human consumption of selenium comes from a variety of sources, including nuts, milk, meat, fish, and eggs. More than 66% of selenium intake in American diets comes from meat, milk, and eggs. See Table 2 for percentages of total selenium intake in common food items.

TABLE 2

Selenium Intake from Common Foods

| Food | % of Total Se Intake |
| --- | --- |
| Meats | 26 |
| Dairy | 22 |
| Eggs | 18 |
| Fish | 12 |
| Cereals | 16 |
| Vegetables, Nuts, etc. | 6 |

The most common form of selenium for human supplementation is selenomethionine. (Schrauzer, Feed Tech). Because animals and humans are unable to synthesize selenomethionine, virtually all selenium in animals and humans is obtained from the diet. In the United States, the recommended daily allowance ("RDA") for adults is 55 micrograms per day. Most humans do not meet the RDA of selenium. Selenium supplementation is not common practice for most adults. Therefore, in order to reach the RDA a variety of selenium-rich sources of food must be consumed, including: organ meats and seafood (0.4-1.5 micrograms per gram); muscle meats (0.1-0.4 micrograms per gram); cereals and grains (less than 0.1 to greater than 0.8 micrograms per gram); dairy products (less than 0.1 to 0.3 micrograms per gram); and fruits and vegetables (less than 0.1 micrograms per gram). Of these sources of selenium in food products, meat and seafood are generally known to be more reliable sources of selenium, in comparison to plant products.

Ongoing health and nutrition studies show that dietary intake of selenium varies greatly among diverse populations. For example, a significant factor determining the intake of selenium from food and meats is the amount of meat a person intakes. The lowest selenium intakes are generally found in populations following vegetarian diets. Moreover, vegetarians living in areas where plants are grown in soil consisting of low selenium show even lower selenium intakes from their diet and are at an increased risk of becoming selenium deficient.

Clinical trials have shown that selenium's effectiveness as an antioxidant and anticancer agent is found at doses of approximately 200 micrograms per day. (See Clark et al.; Wellness Lifestyles, Inc., Petition to FDA for Health Plans Relating to Selenium and Reduction of Risk of Cancers).

In considering health claims allowable by the Food and Drug Administration, the agency recognized the lowest-observed adverse effect level of selenium intake as 900 micrograms per day and the no-observed adverse effect level of selenium as 800 micrograms per day. Therefore the FDA has taken a more conservative dosing schedule for selenium supplementation in concluding that 400 micrograms per day is the upper limit of selenium from food and supplements likely to pose no risk of adverse health effects in almost all people. As a result, the FDA concluded that the use of selenium as a dietary supplement at levels no greater than 400 micrograms per day was safe and lawful (taking into consideration an estimated 100 micrograms per day a person might consume from food sources).

Additional research is ongoing to determine the optimal levels of selenium and selenoproteins necessary to be beneficial for cancer and other diseases. (Rayman, Lancet, Vol. 356, 2000). Rayman's review article on the importance of selenium to human health cautions that a safe daily intake of selenium for human use is approximately 15 micrograms per kilogram body weight per day.

Field of Selenium Use in Bovine

Figure 7:
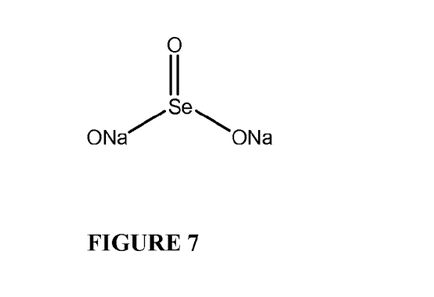
FIG. 7 illustrates the molecular structure of inorganic selenium, sodium selenite, used in cattle supplements.
Figure 8:
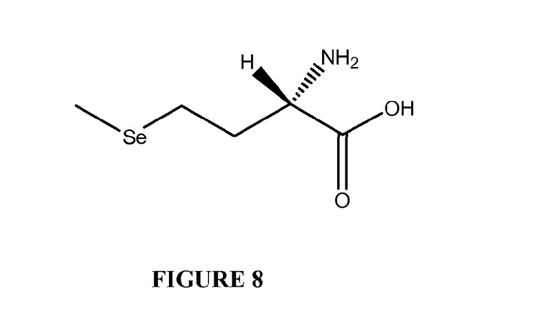
FIG. 8 illustrates the molecular structure of one of the most common forms of organic selenium found in feedstuffs and in selenium yeast, selenomethionine.
Figure 9:
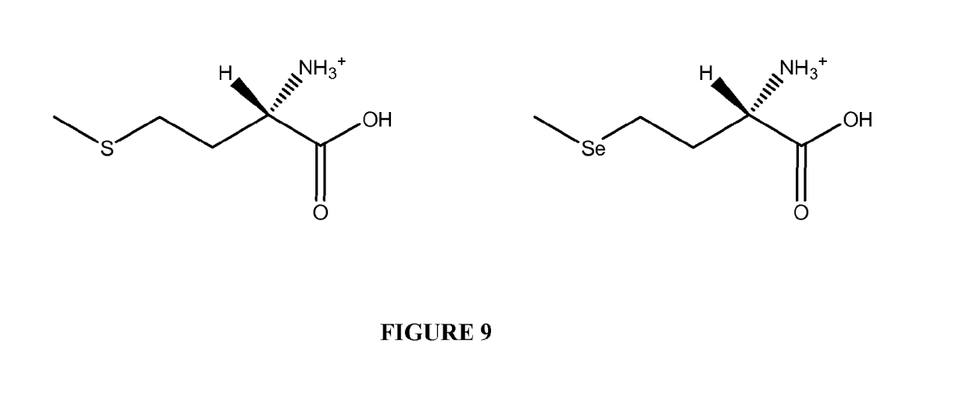
FIG. 9 illustrates the chemical interchangeability of sulfur and selenium and how elemental selenium can be made into organic selenium.

Beef and other livestock animals are often given various forms of supplements in order to promote the animals' health and to achieve desirable meat products upon slaughter. Most often, supplementation with trace minerals, vitamins or other feed additives to livestock are formulated to provide the least expensive forms of supplementation to food animals. This generally results in animals being supplemented with the most inexpensive forms of trace minerals, which are the metallic or "inorganic" forms, such as oxides and sulfates. FIG. 7 shows the molecular structure of how selenium is typically supplemented in the form of sodium selenite. More importantly, FIG. 8 illustrates the molecular structure of organic L-selenomethionine. There are significant differences in bioavailability of trace minerals depending on the chemical form delivered. The relative bioavailability of sodium selenite in comparison to selenomethionine is 100 (baseline) and 245, respectively. See Table 3, according to Henry & Ammerman (1995).

TABLE 3

| Source | Bioavailability |
| --- | --- |
| Sodium Selenite | 100 |
| Cobalt Selenite | 105 |
| Selenomethionine | 245 |
| Selenium Enriched Yeast | 290 |

Organic trace minerals, such as selenium, zinc, copper, manganese, and cobalt are a member of a large class of chemical compounds whose molecules contain carbon. There is often very low bioavailability of inorganic trace minerals to cross the gastrointestinal walls of food animals and still lower distribution in the blood stream and throughout the tissues of the animal. Such decreased distribution, absorption and bioavailability are generally a result of adhering to a least cost approach by animal producers as inorganic trace minerals are considerably less expensive. As a result, livestock mortality has been trending higher in the last 15 years. Loneragan et al. (J Am Vet Med Asso, 219:1122-1127 (2001)) showed mortality ratio increased from 10.3 deaths/1,000 cattle in 1994 to 14.2 deaths/1,000 cattle in 1999 which amounts to approximately 6.1% annual increase in mortality rate. (P=0.09). Respiratory disease or pneumonia has been increasingly implicated in the cause of increasing mortality. It is widely believed that depletions or deficiencies of various nutrients, including trace minerals, are compromising immunity in food animals, such as bovine.

Research relating to antioxidant use in animals through the supplementation of selenoproteins has shown a variety of improvements and benefits in an animal's health, performance and production. For example, selenoproteins have demonstrated improved immune response in neonatal livability, both male and female fertility, and decreased iron toxicity in neonates. However, such improvements in an animal's health, performance and production focus solely on the direct benefits to the animals supplemented with various forms of selenoproteins. These studies do not contemplate or suggest any beneficial effects as a result of human consumption of such supplemented animals' meat.

Beef, pork, and milk normally contain about 0.03 to about 0.06 ppm (mg/kg). However, the amounts of selenium required to obtain antioxidant and anticancer benefits in humans are significantly higher (from about 3-6 times greater) than the amounts which can be obtained by consuming reasonable amounts of cow's milk, beef, and pork. It is reasonable to say that cow's milk, beef, and pork while providing a large percentage of dietary selenium the human diet, does not contain enough selenium to provide the benefits of improved immune function, anticancer effects and other physiologic improvements. As a result, there is a need for selenium enhancement of meat products to be consumed by humans in order to provide beneficial antioxidants and anticancer effects when combined with the selenium consumed in the average human diet.

Figure 1:
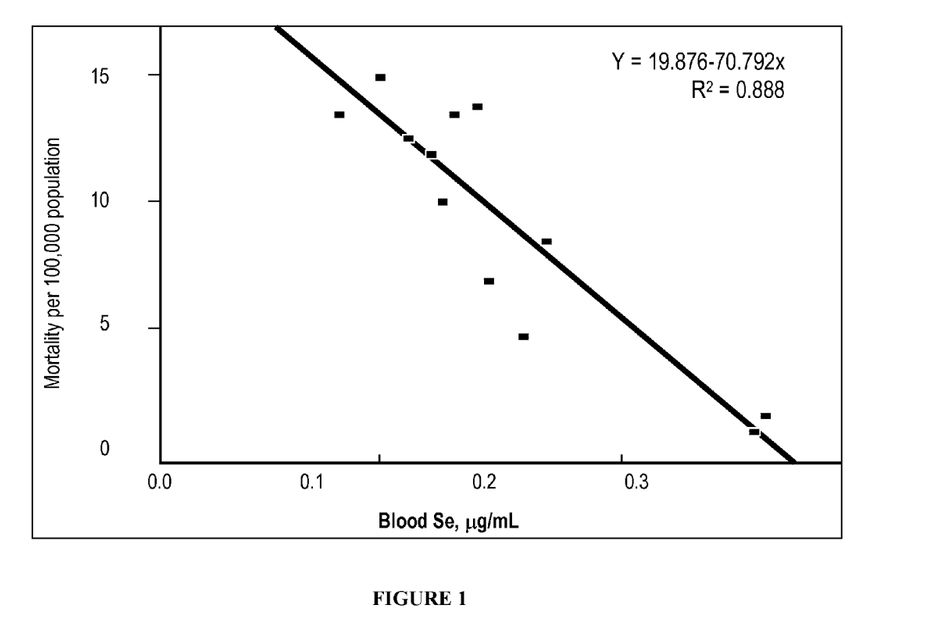
FIG. 1 illustrates the age-corrected prostate cancer mortalities in thirteen countries in comparison to the blood concentrations of selenium of healthy subjects, demonstrating that the mortality per 100,000 population decreases as blood selenium concentrations increase, according to Schrauzer et al. (1979).
Figure 2:
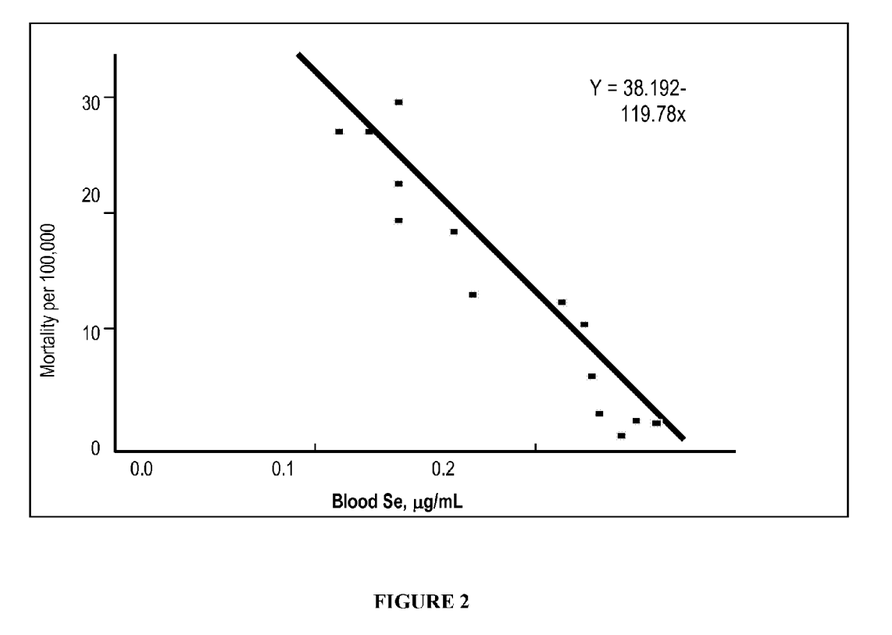
FIG. 2 illustrates the age-correlated breast cancer mortalities in thirteen countries in comparison to the blood concentrations of selenium of healthy subjects, illustrating the mortality per 100,000 population decreases as blood selenium concentrations increases, according to Schrauzer et al. (1979).
Figure 3:
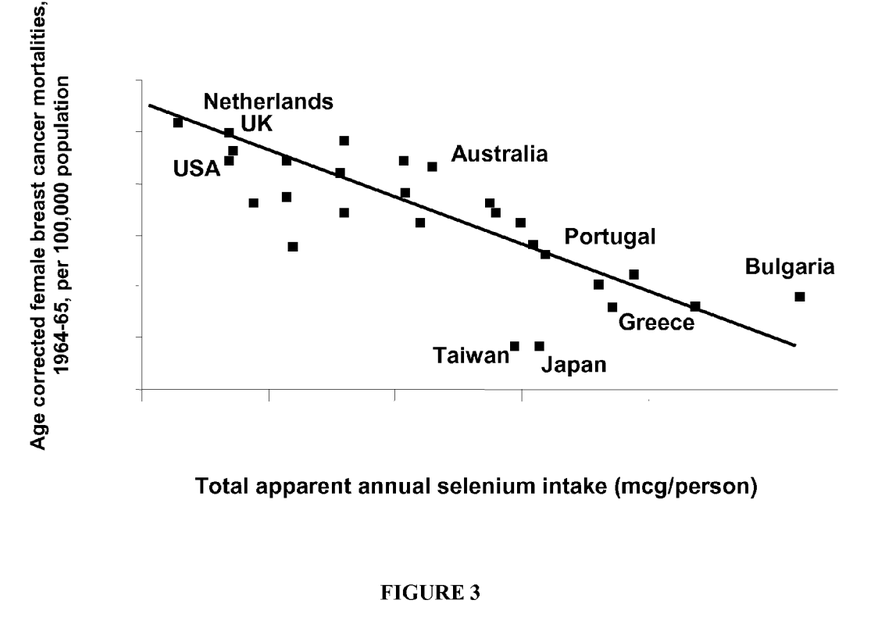
FIG. 3 illustrates the relationship of selenium intake and breast cancer mortalities in various countries, demonstrating the number of female breast cancer mortalities per 100,000 population decreases as the total apparent annual selenium intake per person increases, according to Schrauzer et al. (1979).
Figure 4:
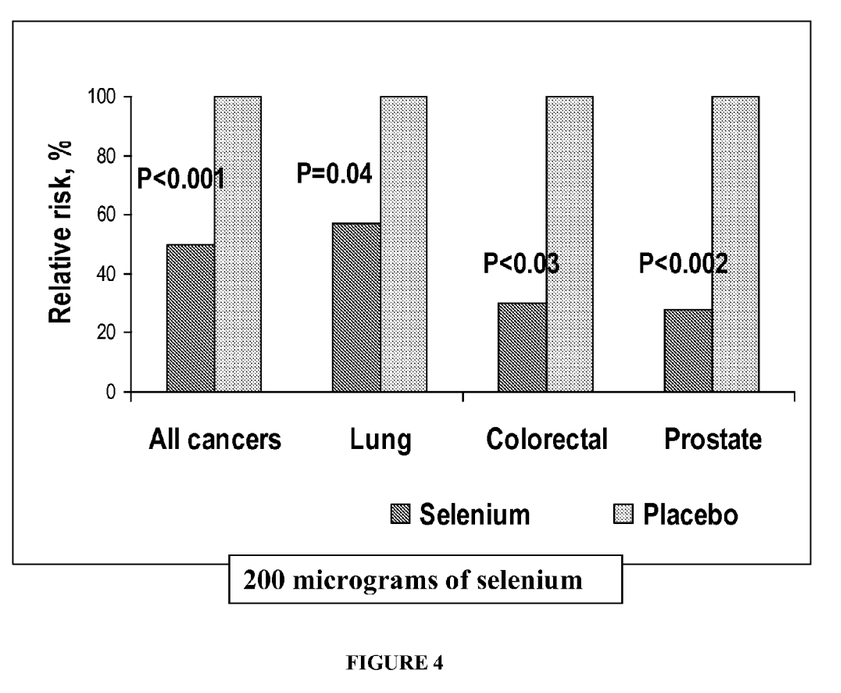
FIG. 4 illustrates the percentage of relative risk of developing all cancers, lung cancer, colorectal cancer and prostate cancer increases in placebo groups, in comparison to groups receiving 200 micrograms of selenium yeast, according to Clark et al. (1996). The difference in relative risk of developing all cancers is statistically significant at $P<0.001$.
Figure 5:
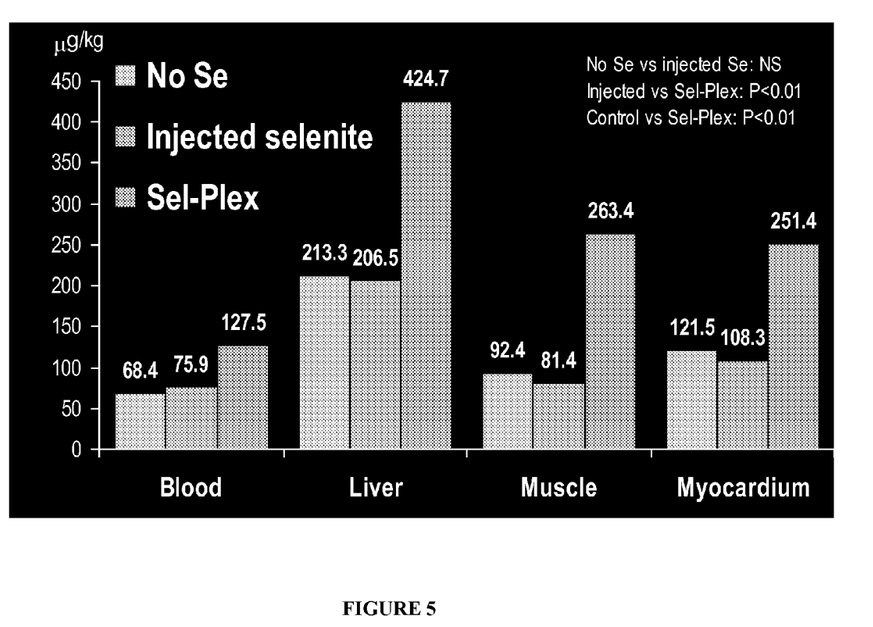
FIG. 5 illustrates the statistically significant increase in average parts per million selenium concentration in comparison to control given to thirty different samples of cattle, according to Pavlata et al. The figure demonstrates that if a person were to eat approximately 450 grams of selenium beef containing the average 0.143 parts per million selenium concentration in the beef a person would consume approximately 65 micrograms per day of selenium (exceeding the 100% recommended daily allowance of selenium).

Supplementations for the purpose of improving an animal's health have traditionally utilized inorganic sources of selenium. However, data has demonstrated that organic selenium is less toxic than inorganic selenium. It has been shown that constant intakes in a nutritional range of selenium, through the supplementation of organic selenium, results in tissue selenium levels increasing until a steady state has been established, allowing effective supplementation while preventing the buildup to toxic levels. (Schrauzer, G. N., Selenomethionine: A Review of its Nutritional Significance, Metabolism and Toxicity, J. Nutr. 130:1653-1656). FIG. 5 shows the increased perfusion to various tissues of the animal, differing based on the administration of an organic versus an inorganic form. In all tissues, the organic selenium has the greatest concentration.

Figure 10:
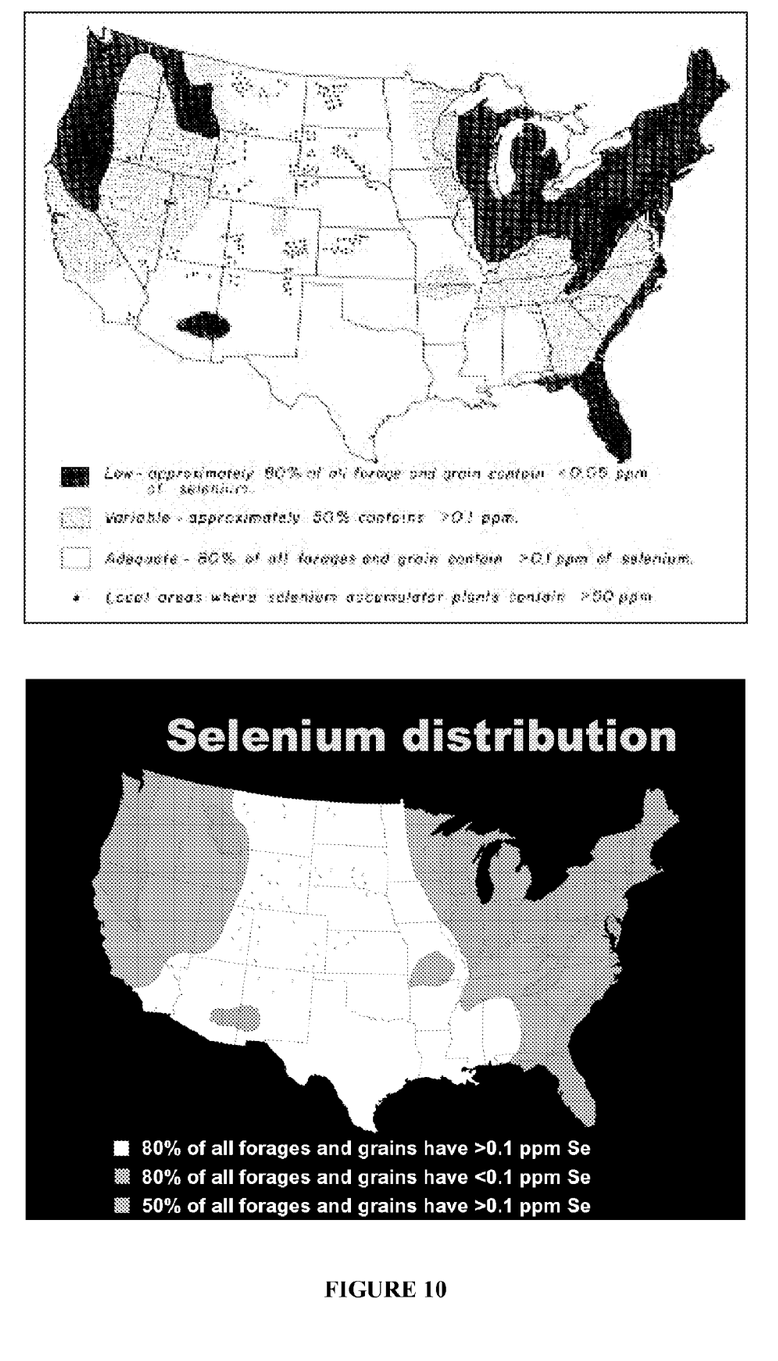
FIG. 10 illustrates the selenium distribution in the soils of North America, illustrating the elevated levels in the Dakotas and the mountain states in comparison to the Great Lakes area.

It is known that the selenium status of bovine can be increased by feeding only feedstuffs naturally high in selenium (i.e., organic form). The amount of selenium fed to bovine for purposes of supplementation or enhancement in food sources in directly correlated to the selenium content of the soil where such feed is grown. (See Wellness Lifestyles, Inc. Petition to FDA for Health Plans Related to Selenium and Reduction in the Risk of Cancers). Selenium enters a food chain through incorporation into plant proteins as amino acids L-selenocysteine and L-selenomethionine. However, there are only certain parts of North America where soil selenium is adequate enough to allow much uptake by plants grown for animal feed (including: North and South Dakota; Montana; and Alberta, Canada). See FIG. 10. It is generally accepted that most of the areas where food animals are produced in the United States have very little selenium left in the soils. Therefore, it is not practical in the United States to rely only on selenium in the feedstuffs (i.e., corn, hay, soybeans) to meet the minimum requirements.

Figure 6:
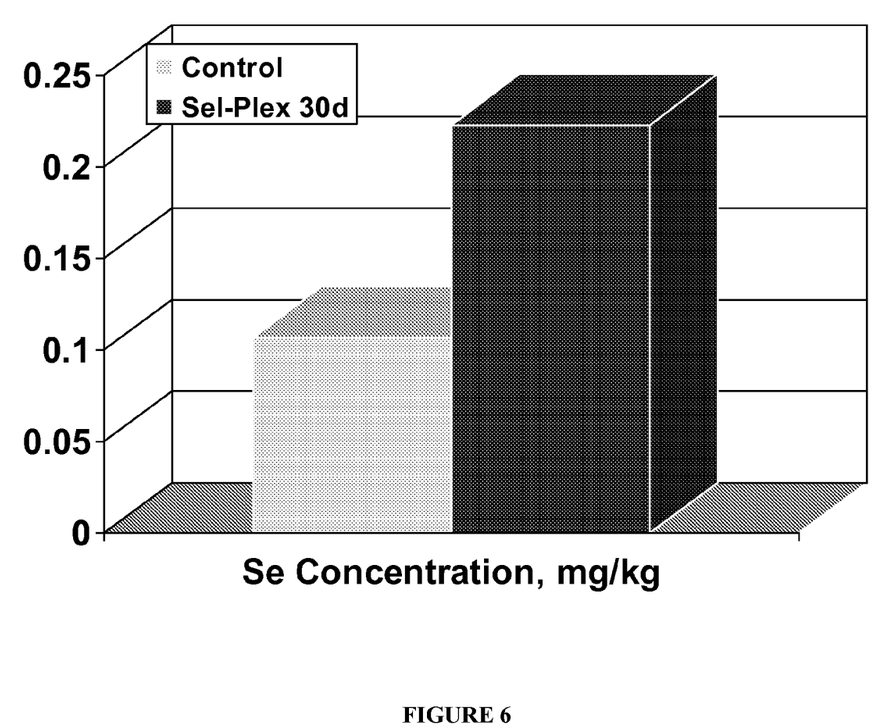
FIG. 6 illustrates the increase in selenium content (mg\kg) in beef after 30 days administration of selenium yeast in comparison to a control diet, according to Simek et al.

Pavlata et al. have shown that oral administration of organic selenium results in higher tissue concentrations than intramuscular injection of inorganic selenium. See FIG. 6. However, such research is merely aimed at demonstrating the biological effects that trace elements have on animals' health and performance. For example, Pavlata et al. look to trace elements for feed additives as replacements for antibiotics and hormonal growth stimulants. The results show that long-term oral administrations of organic selenium resulted in higher blood selenium concentrations than intramuscular injection of an inorganic selenium-containing compound. See FIG. 5. Such therapies were tested and are intended to be used solely for treating selenium deficiencies in animals. As a result, those skilled in the art traditionally use inorganic selenium forms, such as sodium selenite, for use in premixes, supplements and complete feed products to be ultimately sold to producers to supplement selenium-deficient diets in animals, such as cattle. There is no focus or interest in the use of organic selenium sources to provide an enhanced diet for beef cattle for the purpose of supplementing the human diet for selenium deficiencies and the prevention of diseases such as cancer.

Some focus has been placed on organic sources of selenium. The fermentation of yeast is a source that can form organic selenium and can be used to supplement livestock feed. It would be advantageous and solve a long-felt problem in the art of human cancer prevention and therapy, and other human pathologies, to develop methods to enhance the diet of bovine through the use of organic selenium, such as fermented yeasts, to ultimately pass along for human consumption meat with enhanced selenium content.

There is, therefore, a pressing need for a new, safe, efficient and non-invasive method of administering to humans, bovine meat that is enhanced with selenium to not only meet the RDA, but also enhance one's selenium intake to receive the beneficial immune and anticancer effects of selenium. Therefore, it would be advantageous to have a method of increasing the selenium content in beef. It would also be advantageous to develop beef with increased content of other organic minerals, such as zinc, copper and manganese.

BRIEF SUMMARY OF THE INVENTION

It is the object of the present invention to obtain improved meat products produced by the methods of increasing the selenium content of beef by a feeding a special enrichment diet to beef cattle.

A further object is to obtain improved meat products obtained as a result of feeding a protocol of a special enrichment diet to beef cattle to increase the selenium level in beef for human consumption.

It is a further object of the present invention to disclose novel meat compositions having increased Vitamin E retention, reduced TBARS and/or improved water holding capacity in comparison to meat products not obtained from beef cattle fed said special enrichment diet.

Providing consumers a variety of consumer food products with the supplementation of antioxidants and cancer-preventing ingredients is a desired and advantageous method of decreasing a person's risk of cancer and other ailments. Therefore, the methods of the present invention provide means for decreasing a human's risk of cancer by providing an enhanced source of bovine meat with increased selenium content sufficient to meet RDA as well as enhanced amounts required for antioxidant and cancer-preventing levels.

Organic forms of selenium are disclosed herein to achieve the objects of the present invention. Organic selenium from fermented yeast provides an effective means to reverse the trend of selenium deficiencies in humans and provide selenium enhanced dietary sources. Because few humans take daily supplements for selenium to reach its RDA, and because many areas are increasingly becoming selenium-depleted, the methods of the present invention provide an alternative to daily supplements of selenium. Accordingly, it is an object of the present invention to increase selenium content in meat products consumed by humans to supplement the increasingly selenium-deficient diet of humans.

The selenium content of beef can be significantly increased by feeding beef cattle the special enriched diet of the present invention for 150 consecutive days. The enriched diet includes 3.0-4.0 mg of selenium derived from an organic form, such as selenium yeast. For maximum benefit to increase the selenium content in the muscle tissue of the beef cattle, the special enriched diet can be fed for as little as 120 consecutive days or throughout the lifespan of the cattle. A feeding range of 120-180 consecutive days just prior to slaughter is a preferred method. Ideally, to increase the selenium content in beef, the disclosed special enriched diet for beef cattle may be fed throughout the animal's life. However, beef cattle can be started on the special enriched diet using the feeding protocols as disclosed to achieve the results of higher selenium in beef.

Preferred organic selenium utilized in the methods of the present invention is Sel-Plex® (Alltech, Inc., 3031 Catnip Hill Pike, Nicholasville, Ky. 40356). Sel-Plex® is an organic selenium yeast produced by *Saccharomyces cerevisiae* (CNCM 1-3060). Sel-Plex® provides the same forms of selenium as are naturally occurring in organic plants. This is extremely beneficial as organic selenium provides a more easily digestible form of selenium in comparison to inorganic forms. Organic selenium is also better retained by an animal, causing an animal to build nutrient reserves against periods of increased demand, without risking unwanted toxicities in an animal. See Table 4 showing increased selenium content in beef tissue from organic selenium of the special enrichment diet of the present invention in comparison to a control group. These cattle were sourced in the Great Lakes region of North America, an area known to be deficient in soil selenium.

TABLE 4

| Organic proprietary supplement | | Control | |
| --- | --- | --- | --- |
| ID | ppm Se | ID | ppm Se |
| 3 | .157 | 101 | .069 |
| 5 | .149 | 110 | .059 |
| 9 | .189 | 118 | .057 |
| 15 | .165 | 120 | .034 |
| 16 | .127 | 121 | .049 |
| 17 | .159 | 124 | .084 |
| 18 | .135 | 125 | .058 |
| 19 | .161 | 129 | .073 |
| 23 | .114 | 131 | .075 |
| 32 | .125 | 132 | .064 |
| 34 | .125 | 134 | .006 |
| 35 | .118 | 137 | .065 |
| 37 | .135 | 139 | .095 |
| 42 | .130 | 141 | .050 |
| 44 | .157 | 149 | .065 |
| Average | .143 | Average | .064 |
| # Samples | 15 | # Samples | 15 |
| P = | 0.000000024 | | |

The organic selenium also results in increased quality of the meat product, including for example, decreased drip loss, improved retail display and increased shelf life. As a result, the product for human consumption demonstrates improved quality according to a variety of measurements, resulting in a more desirable product. The desirable product is a result, at least in part, to the complete removal of all inorganic minerals and elements from the animal feed supplementation comprising the special enriched diet. The enriched diet further includes organic forms of zinc, copper and manganese to produce the improved quality in the beef for human consumption.

Sel-Plex® is the only organic selenium yeast product that has been reviewed and approved by the FDA. Selenium yeast has received allowance for use in poultry, swine, goat, sheep, equine, beef and dairy feeds, and canine diets. The FDA permitted the safe use of Sel-Plex® as an organic selenium supplement for beef in September of 2003. Sel-Plex® also received authorization as a nutritional feed additive for use in all species diets, from the European Union (EU) under EU regulation 1750/2006.

However, other selenium yeast products or organic selenium compounds may also be used to achieve similar results. Other organic selenium compounds with superior bioavailability include but are not limited to selenomethionine, selenocysteine, and zinc-L-selenomethionine. The relative bioavailabilities of selenium compounds sodium selenite, cobalt selenite, selenomethionine are 100 (which is a baseline), 105 and 245, respectively. (Henry & Ammerman, 1995). In comparison, selenium yeast is a mixture of many difference organic selenoaminoacids, selenopeptides, and selenoproteins which has the highest of 290, and therefore represents a preferred embodiment for the feed compositions of the present invention. The preferred embodiment of organic forms of trace minerals can increase absorption across the intestines by 250-290%.

The selenium-enriched yeast, like all plants, incorporates the selenium into proteins and amino acids. Pavlata et al. demonstrated a use of injected inorganic selenium in comparison to oral organic selenium in demonstrating the distribution of selenium in various tissues, including blood, liver, muscle and myocardium. The purpose of this study was to determine the difference in distribution of selenium beyond intestinal absorption, which explains the injection of the inorganic selenium. See FIG. 5. Use of organic selenium yeast demonstrated statistically significant increase in tissue concentration in comparison to both control and injected selenite in all tested tissues, including muscle tissue. Such demonstration of increased bioavailability and distribution of organic selenium demonstrates that inorganic selenium should be disfavored as oral organic forms of selenium are capable of accomplishing statistically significant increases in tissue distribution of selenium. Therefore, oral compositions for organic selenium supplementation represent a desirable method of administering selenium to both humans and animals. The oral compositions further include organic zinc, copper and manganese. The replacement of inexpensive and oxidative inorganic forms of zinc, copper and manganese similarly results in increased bioavailability and distribution of the organic minerals, yielding an improved meat product.

The novel feed of the present invention is a conventional feed for beef cattle which contain 0.3 mg/kg dry matter ("DM") of organic selenium. The selenium added to the feed is in the form of organic selenoaminoacids and selenoproteins derived from selenium yeast. The oral administration of organic selenium in the form of organic selenoaminoacids and selenoproteins also presents numerous additional benefits to the bovine producers. For example, benefits are seen as a result of increased ease of application and use, decreased cost and improved convenience of administration.

The special enhanced diet of the present invention removes all inorganic forms of selenium salts from the feed. Inorganic forms of zinc, copper, iodine, manganese, and cobalt are also removed from the feed and replaced with organic trace minerals of zinc, copper, iodine, manganese, and cobalt in addition to the selenium. The removal of all inorganic trace minerals provides an important advantage to the special enriched diet. The all organic form of the special enhanced diet allows the meat to not only have a high content of selenium, but also enriched with organic trace minerals that are provided in a consistent form which will be beneficial to the health of human consumers. The beef product for human consumption contains exclusively organic minerals and supplements.

There are also numerous additional benefits to the quality of the meat derived from cattle fed the conventional feed of the present invention. Organic selenium and organic trace mineral administration to cattle also results in reduced drip losses in the meat, reduced water loss in vacuum packaging, increased shelf life and increased muscle selenium, manganese, copper and zinc concentrations. These benefits are derived in addition to the significant benefits seen in preventing cancer rates in humans due to enhancing selenium levels. The findings of the present invention indicate that the removal of all forms of metallic and/or inorganic forms of trace minerals is required to realize the improvements in meat quality.

DETAILED DESCRIPTION OF THE INVENTION

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, processes and examples described in the description of the invention are illustrative only and not intended to be limiting to the scope of the invention in any manner. Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims.

The present invention relates to improved meat products obtained from methods of increasing the selenium content in beef. In addition the invention relates to meat compositions having various improvements in shelf-life, stability and nutritional content as a result of the special enriched diets for the beef. The special enrichment diet fed to beef cattle includes organic selenium yeast (a preferred embodiment of the present invention uses the selenium yeast Sel-Plex®) in addition to various enrichment contents, including Vitamin A, D, and E, organic zinc, copper, manganese and cobalt. The special enrichment diet removes all inorganic and metallic forms of minerals and trace elements from the composition for achieving optimum improvements in beef quality.

Applicant provides a special enrichment diet for beef cattle providing numerous benefits, in addition to enhanced selenium concentration in meat tissue, to be passed along for human benefits upon consumption. Human consumption of beef products enriched with organic selenium, in addition to organic zinc, copper and manganese provides increased intake of the organic minerals, namely selenium providing anticancer effects. Moreover, the enrichment diet does not contain any supplements comprising sodium selenite (inorganic form of selenium), sulfates or oxides (inorganic trace minerals), or any animal byproducts. The special enrichment diet also provides improved meat quality based on measures of decreased drip loss and decreased water loss.

In a preferred embodiment of the method of the present invention for feeding beef cattle, the selenium content of beef can be significantly enhanced by feeding to beef cattle the special enriched diet for as little as about 120 consecutive days. The special enriched diet includes 3.0-4.0 mg of selenium derived from an organic form (by administering 0.3 mg/kg dry intake matter to beef cattle), preferably selenium yeast. For maximum benefit to increase the selenium content in the muscle tissue of the beef cattle, the special enriched diet can be fed for as little as 120 consecutive days with a preferred feeding range of 120-180 consecutive days just prior to slaughter. A further preferred feeding range consists of feeding beef cattle throughout its life with the special enriched diet.

The special diet is further enriched with organic trace minerals and vitamins. In addition to the selenium provided from an organic source such as selenium yeast, the diet is completely rid of all inorganic forms of trace minerals. All trace elements having an oxidative effect on the end product are removed. Any inorganic trace mineral compounds are replaced with organic trace minerals including, for example, zinc, copper and manganese. The organic components result in an enriched diet absent any metallic forms, such as the poorly bioavailable concentrated zinc oxide. Moreover, the enriched diet removes any sulfate forms of the trace elements. The resulting product is an organic enriched diet that is highly bioavailable and distributes throughout the beef cattle tissue.

The special enriched diet fed to beef cattle as disclosed by the present invention will enrich the meat to provide selenium in amounts exceeding the RDA of selenium. The RDA for an American adult is 55 micrograms of selenium. The average selenium content of meat from cattle fed an enrichment diet, contains an approximately 0.3 ppm (300 mcg/kg meat). Accordingly, the consumption of an 8 oz. steak would deliver an estimated 70 mcg of selenium, in addition to the added organic trace minerals and vitamins. The one serving of beef far exceeds the RDA of selenium, and will contribute to the estimated 200 mcg of selenium required to receive selenium's anticancer effects. Therefore, the addition of an enhanced selenium-containing beef product to an average adult diet wherein other natural sources of selenium are included, the average person can quickly achieve the recommended 200 mcg of selenium to realize all of its intended health benefits. The addition of the selenium-enhanced beef to the diet prevents a person from having to take daily supplements of selenium to achieve the desired results and ensures that no selenium deficiencies occur.

The present invention results in beef obtained by the methods of the present invention that contain much greater levels of selenium than those achieved under normal feeding practices, and is a sufficient quantity to provide antioxidant, improved immune functions and anticancer effects in a human after consumption.

Moreover, there are also numerous additional beneficial outcomes in supplementing beef with organic selenium, zinc, copper and manganese through feeding practices, such as the present invention. The addition of organic selenium and organic minerals such as zinc, copper and manganese results in reduced drip loss, reduces water loss in vacuum-packaged beef, improves oxidation for aged steaks on retail display, increases shelf life as well as significantly increases the selenium content in beef. The use of only organic selenium and trace minerals and vitamins in the methods of the present invention result in the replacement of inorganic forms of the trace minerals.

The reduction in drip loss from bovine meat is illustrated in Tables 5 and 6 wherein standard cuts of beef were measured to determine the difference in percentage of drip loss. Control cuts are set forth in Table 5. The cuts of been were weighed when sold (i.e., box weight) and then weighed again at the consumer level after packaging has been opened and any water and/or drip is removed. Table 6 measured the same cuts of beef that were fed the special enrichment diet of the present invention.

TABLE 5

Baseline Drip Loss Beef Test

| | Box Weight-No-Selenium | Actual weight | % of shrink |
| --- | --- | --- | --- |
| Chucks | 47.8 | 47.05 | 0.015690377 |
| Clods | 68.9 | 68.15 | 0.010885341 |
| Super trim | 63.8 | 61.95 | 0.028996865 |
| Strips | 11.3 | 11 | 0.026548673 |
| Eye-o-Round | 56.3 | 55.2 | 0.019538188 |
| Inside Rounds | 48.9 | 47.5 | 0.028629857 |
| Outside Rounds | 47 | 46.1 | 0.019148936 |

TABLE 6

Selenium Drip Loss Beef Test

| Item | Box Weight-Selenium | Actual weight | % of shrink | Difference |
| --- | --- | --- | --- | --- |
| Chucks | 48.6 | 48.45 | 0.00308642 | −0.0126 |
| Clods | 69.5 | 69.35 | 0.002158273 | −0.00873 |
| Super trim | 67.9 | 66.7 | 0.017673049 | −0.01132 |
| Strips | 13.2 | 13.05 | 0.011363636 | −0.01519 |
| Eye-o-Round | 60.2 | 59.45 | 0.012458472 | −0.00708 |
| Inside Rounds | 49.1 | 47.75 | 0.027494908 | −0.00113 |
| Outside Rounds | 49.3 | 49.05 | 0.005070994 | −0.01408 |
| | | | | −0.01002 |

The difference in percentage of drip loss from the control group to the selenium group (fed the special enriched diet) is set forth in Table 6. The beef that was fed the special enriched diet demonstrated an average of 1% reduction in drip loss, and decreasing as much as 1.5%. This amount outpaces the improvements in drip loss of Simek et al. wherein after only 30 days of organic selenium supplementation an average of less than 0.5% decrease in drip loss was observed. The control and test groups were fed the special enriched diet of organic selenium, copper, manganese and zinc, yielding an unexpected increase in the decrease of average rates of drip loss.

The bovine meat having improved drip loss percentages were found in cattle from areas of Minnesota and Northwest Iowa, wherein the soil is generally selenium rich. Despite the preexisting level of selenium, due to the level of selenium found in the soil in these areas, the enhancement of the cattle's diet still yielded a significant decrease in percentage of drip loss. Accordingly, cattle in areas of selenium deplete soils are expected to yield an even greater increase in the average percentage of decrease of drip loss.

The results of feeding the special enhanced diet of the present invention to beef cattle illustrate that cattle with the lowest initial selenium status (i.e., beef cattle in geographic regions with low or selenium deplete soils) receive the greatest increase in selenium in muscle tissue. There is evidence suggesting there is a selenium equilibrium level when enhancing beef cattle, namely from about 0.3 to 0.5. Therefore, the methods of the present invention may yield the most benefit in beef cattle with initially lower selenium status.

Moreover, by using organic selenium, rather than an inorganic form such as sodium selenite (wherein selenium is ionically bonded to a sodium molecule) (FIG. 7), there is not an ionized form of selenium disassociated in the rumen of the beef cattle. The eradication of the ionized forms of selenium and other minerals, such as zinc, copper and manganese works to increase the quality of the meat that is rendered from the beef cattle. The organic form of selenium used from yeast sources circulates as selenomethionine (FIG. 8), which is more bioavailable and is therefore subject to much greater distribution. Such effective distribution is the result of selenium circulated through the beef cattle as an amino acid (FIG. 5).

Additional benefits of the improved meat products include increased Vitamin E retention and reduced TBAR. Without being limited to a particular theory of the invention, the providing of the special enrichment diet increases selenium content of the meat which further promotes the retention of Vitamin E content in the meat. Enhanced Vitamin E provides numerous benefits with respect to decreased oxidative damage of the meat. This is demonstrated through the decrease in TBAR (lipid oxidation of the meat) set forth in the Examples.

The meat products of the invention beneficially provide both improved oxidative condition and deceased tissue damage.

The invention has been described with reference to various specific and preferred embodiments and techniques. However, it should be understood that many variations and modifications may be made while remaining within the spirit and scope of the invention. In particular, it is to be understood that the present invention contemplates variations in the organic components of the special enriched diet, process parameters for making the special enriched diet, including temperature, time, pH, salts, manufacturing techniques, drying or preparation techniques, and selenoproteins of interest.

All publications in this specification are indicative of the level of ordinary skill in the art to which this invention pertains. All publications are herein incorporated by reference in its entirety to the same extent as if each individual publication was specifically and individually indicated by reference.

EXAMPLES

This invention can be better understood by reference to the following examples, which are intended to be illustrative of embodiments of the invention, but non-limiting in terms of scope of the invention. It will be appreciated by those skilled in the art that other embodiments of the invention may be practiced without departing from the spirit and the scope of the invention, the scope of which is defined by the appended claims.

Example 1

An example of a special enriched diet for beef cattle is shown herein:
Novel Premix

| Ingredient | % Dry Matter | Pounds/Ton |
|---|---|---|
| Ground rice hulls | 0.133 | 2.66 |
| Vitamin E 50% | 1.101 | 22.03 |
| Vitamin D3 SD | 0.018 | 0.35 |
| Vit A1000/D200 | 0.055 | 1.1 |
| Ethylenediamine Dihydriodide (EDDI) | 0.01 | 0.19 |
| Suppli-K (KCL) | 31.3 | 626 |
| Magnesium Oxide 54% | 19.3 | 386 |
| Sodium Bicarbonate | 38.6 | 772 |
| Organic zinc | 2.631 | 52.63 |
| Organic manganese | 1.993 | 39.86 |
| Organic copper | 0.997 | 19.94 |
| Mineral oil | 0.75 | 15 |
| Organic cobalt | 0.159 | 3.17 |
| Sel-Plex 2000 ® | | 2.953 |
| Totals | 100% | 59.06 |

Nutrient Specification of Novel Premix

| Calcium | % | 0.543 |
|---|---|---|
| Phosphorous | % | 0.03 |
| Sodium | % | 10.916 |
| Magnesium | % | 10.509 |
| Zinc | ppm | 4000 |
| Manganese | ppm | 2000 |
| Copper | ppm | 1000 |
| Cobalt | ppm | 0.03 |
| Iodine | ppm | 77 |
| Selenium | ppm | 60 |
| Vit A | KIU/# | 250 |
| Vit D | KIU/# | 90 |
| Vit E | IU/# | 2500 |

Total Diet of Animals with the Novel Premix Added

| Feed Name | # Head/Day |
|---|---|
| Ground Limestone | 0.306 |
| Liquid Vegetable Fat | 0.186 |
| Novel Premix | 0.120 |
| Potassium Carbonate | 0.098 |
| Grass Hay | 2.328 |
| Dry Cracked Corn | 9.000 |
| Corn Bran Pellets | 8.000 |
| Corn Distillers Solubles | 10.000 |

The novel premix comprising the special enriched diet for cattle to provide organic selenium, and other minerals, including zinc, copper and manganese, were fed to cattle in high selenium soils areas over varying periods of time before slaughter.

Example 2

The following research was conducted at South Dakota State University. These cattle were sourced from the more selenium rich soils of western Iowa, Minnesota, and the Dakotas. This data demonstrate that even when cattle were sourced from soils with high selenium, the novel enrichment premix still raised the selenium levels in the meat well above 0.3 ppm using the enrichment protocol. There was a 40% increase in meat selenium levels over the control levels.

| Sample | Control Meat | As Received Basis | Sample | Treatment Meat | As Received Basis |
|---|---|---|---|---|---|
| 1 | Total Moisture, % | 70.5 | 1 | Total Moisture, % | 71.2 |
| | Total Dry Matter, % | 29.5 | | Total Dry Matter, % | 28.8 |
| | Selenium, ug/g (ppm) | 0.245 | | Selenium, ug/g (ppm) | 0.311 |
| 2 | Total Moisture, % | 70.5 | 2 | Total Moisture, % | 71 |
| | Total Dry Matter, % | 29.5 | | Total Dry Matter, % | 29 |
| | Selenium, ug/g (ppm) | 0.228 | | Selenium, ug/g (ppm) | 0.355 |
| 3 | Total Moisture, % | 74.2 | 3 | Total Moisture, % | 71.2 |
| | Total Dry Matter, % | 25.8 | | Total Dry Matter, % | 28.8 |
| | Selenium, ug/g (ppm) | 0.258 | | Selenium, ug/g (ppm) | 0.303 |
| 4 | Total Moisture, % | 71 | 4 | Total Moisture, % | 72.2 |
| | Total Dry Matter, % | 29 | | Total Dry Matter, % | 27.8 |
| | Selenium, ug/g (ppm) | 0.242 | | Selenium, ug/g (ppm) | 0.328 |
| 5 | Total Moisture, % | 69.6 | 5 | Total Moisture, % | 71.4 |
| | Total Dry Matter, % | 30.4 | | Total Dry Matter, % | 28.6 |
| | Selenium, ug/g (ppm) | 0.201 | | Selenium, ug/g (ppm) | 0.313 |
| 6 | Total Moisture, % | 72.2 | 6 | Total Moisture, % | 67.6 |
| | Total Dry Matter, % | 27.8 | | Total Dry Matter, % | 32.4 |
| | Selenium, ug/g (ppm) | 0.222 | | Selenium, ug/g (ppm) | 0.314 |
| 7 | Total Moisture, % | 72.9 | 7 | Total Moisture, % | 73.8 |
| | Total Dry Matter, % | 27.1 | | Total Dry Matter, % | 26.2 |

-continued

| Sample | Control Meat | As Received Basis | Sample | Treatment Meat | As Received Basis |
|---|---|---|---|---|---|
|  | Selenium, ug/g (ppm) | 0.237 |  | Selenium, ug/g (ppm) | 0.339 |
| 8 | Total Moisture, % | 61.8 | 8 | Total Moisture, % | 69.2 |
|  | Total Dry Matter, % | 38.2 |  | Total Dry Matter, % | 30.8 |
|  | Selenium, ug/g (ppm) | 0.184 |  | Selenium, ug/g (ppm) | 0.299 |
| 10 | Total Moisture, % | 70.4 |  |  |  |
|  | Total Dry Matter, % | 29.6 |  |  |  |
|  | Selenium, ug/g (ppm) | 0.248 |  |  |  |
| 11 | Total Moisture, % | 72.5 |  |  |  |
|  | Total Dry Matter, % | 27.5 |  |  |  |
|  | Selenium, ug/g (ppm) | 0.237 |  |  |  |
|  | Ave Control (ppm) | 0.2302 |  | Ave Treatment (ppm) | 0.32 |

Example 3

The quality and characteristics of improved meat products according to the invention were evaluated. Samples were collected and analyzed from the longissimus muscle of fourteen beef animals. Seven individuals served as un-treated controls and seven animals were treated according to the special enrichment diet of the invention. Longissimus samples were analyzed at day 1, 3, 5, and 7 postmortem for objective color (L*, a*, b*). Samples were also evaluated for oxidation using the TBARS assay. Sample drip loss, cooking loss and shear force were also recorded. Data were analyzed using the PROC GLM procedure of SAS (SAS Inst. Inc., Cary, N.C.). Means were separated using the LSMEANS statement.

The quality of the beef products were evaluated under similar conditions as meat/steaks experience for retail sale to consumers (e.g. placed on a Styrofoam tray with a soaker pad and over-wrapped with a polyvinyl chloride film (PVC)). Trays were placed into a coffin style display case which was maintained at 35.6° F.±1° F., under constant light conditions. The surface of the meat was exposed to (900 to 1365 lux) as recommended by AMSA (1991). Each steak was objectively and subjectively evaluated for color and other attributes during retail display conditions for 7 days. Quality characteristics are summarized in Table 7.

TABLE 7

Least squares means of quality characteristics for longissimus samples.

| Item | Control | Treatment | SEM | p-value |
|---|---|---|---|---|
| n | 7 | 7 |  |  |
| Drip loss, % | 2.02 | 1.78 | 0.22 | 0.4337 |
| Cooking loss, % | 24.03 | 21.74 | 0.67 | 0.0338 |
| Shear force, kg | 4.16 | 3.93 | 0.40 | 0.7033 |
| TBARS[a], ng MDA/g | 32.38 | 31.00 | 1.88 | 0.6121 |

No statistically significant differences were detected between control and treated samples for drip loss, TBARS or shear force. However, it is noteworthy that treated samples had numerically less drip loss, lower shear force and less oxidation all of which are positive traits and warrant further investigation with larger samples sizes. Cooking loss was significantly lower (P=0.0338) for treated samples indicating less moisture was lost from the sample during cooking. This outcome should produce a juicier product when consumed.

The small sample size also demonstrated a reduction in TBARS assay, which is a well-recognized assay (thiobarbituric acid reactive substances assay) for assaying the lipid degradation within meat products. Although not statistically significant due to small sample size, results did corroborate earlier statistically significant observations of lower TBAR. The reduction in TBARS provides a significant benefit for the quality of the meat. Improvement in the reduction in TBARS beneficially can provide an indicator of increased shelf-life according to the invention.

Objective color data is summarized in Table 8. L*, a* and b* measure lightness, redness and yellowness respectively.

TABLE 8

Least squares means of objective color measurements (L*, a*, b*) a for longissimus samples

| Item | Control | Treatment | SEM | p-value |
|---|---|---|---|---|
| n | 7 | 7 |  |  |
| Day 1 |  |  |  |  |
| L* | 35.146 | 35.923 | 1.09 | 0.6266 |
| a* | 20.991 | 18.606 | 0.92 | 0.0915 |
| b* | 56.00 | 4.734 | 0.74 | 0.4243 |
| Day 3 |  |  |  |  |
| L* | 34.920 | 37.203 | 1.32 | 0.2444 |
| a* | 25.043 | 22.684 | 0.95 | 0.1043 |
| b* | 8.137 | 7.499 | 0.83 | 0.5952 |
| Day 5 |  |  |  |  |
| L* | 37.570 | 37.224 | 1.36 | 0.8607 |
| a* | 23.723 | 20.984 | 0.787 | 0.0291 |
| b* | 7.551 | 6.233 | 0.64 | 0.1731 |
| Day 7 |  |  |  |  |
| L* | 33.986 | 36.947 | 1.15 | 0.0930 |
| a* | 22.320 | 17.844 | 1.13 | 0.0160 |
| b* | 7.234 | 5.576 | 0.82 | 0.1775 |

[a]L* 0 = black and L* 100 = white;
a* negative values indicate green and positive values indicate red;
b* negative values indicate blue and positive values indicate yellow No differences were detected between control and treated samples for L* or b* measurements indicating no difference in product lightness or yellowness over the storage period. However, control samples had higher a* values at day 5 (P=0.0291) and day 7 (P=0.0160) indicating control samples were more red at days 5 and 7 postmortem. The unexpected significance in color change may be due to treatment diet influencing myoglobin stability or a function of improved overall oxidative stability.

What is claimed is:

1. An improved meat product comprising:
   a meat product with improved oxidative condition produced by the process for increasing selenium content in beef comprising:
   combining organic selenium and organic trace compounds to create a special enrichment diet for beef cattle;
   removing inorganic and/or metallic trace minerals and compounds from said special enrichment diet; wherein said inorganic and/or metallic trace minerals and compounds are selected from compounds having zinc, copper, iodine, manganese and cobalt and combination thereof; and
   feeding said special enrichment diet to beef cattle.

2. The composition of claim 1 wherein said special enrichment diet contains about 0.3 mg/kg of dry matter intake of selenium.

3. The composition of claim 1 wherein said organic selenium is an organic selenium yeast product.

4. The composition of claim 1 wherein said organic selenium is in the form of organic selenoaminoacids and selenoproteins.

5. The composition of claim 1 wherein said inorganic and/or metallic trace minerals are selected from the group consisting of zinc, copper, iodine, manganese, cobalt and combinations thereof, and said organic trace compounds are selected from the group consisting of zinc, copper, iodine, manganese, cobalt and combinations thereof.

6. The composition of claim 5 wherein said special enriched diet further comprises Vitamins A, D, and E.

7. The composition of claim 2 wherein said organic selenium and is fed to beef cattle for at least 120 days.

8. The composition of claim 1 further comprising correlating said selenium intake with the amount of selenium found in soil where said beef cattle are grown.

9. An improved meat product comprising:
   a meat product with improved oxidative condition produced by the process for increasing selenium content in beef comprising:
   combining organic selenium and other organic trace minerals to create a special enrichment diet to feed to beef cattle, wherein said organic trace minerals are selected from the group consisting of Vitamin A, Vitamin D, Vitamin E, zinc, copper, iodine, manganese, cobalt and combinations thereof, and wherein said special enrichment diet does not contain any inorganic and/or metallic trace minerals and compounds; and
   feeding said special enrichment diet to beef cattle.

10. The composition of claim 9 wherein said special enrichment diet contains about 0.3 mg/kg of dry matter intake of said selenium and is fed to beef cattle for at least 120 days.

11. The composition of claim 9 further comprising removing all inorganic and/or metallic forms of trace minerals and compounds from said special enhancement diet.

12. The composition of claim 11 wherein said special enhancement diet includes organic zinc, copper and manganese.

13. The composition of claim 9 further comprising slaughtering said beef cattle, wherein said beef cattle has improved quality features selected from the group consisting of decreased drip loss, improved retail display, increased shelf-life and combinations of the same.

* * * * *